US010881303B2

(12) United States Patent
Zucker et al.

(10) Patent No.: US 10,881,303 B2
(45) Date of Patent: Jan. 5, 2021

(54) DEVICES AND METHODS FOR DETECTING AND MEASURING SYMPATHETIC VASOMOTION

(71) Applicant: Board of Regents of the University of Nebraska, Lincoln, NE (US)

(72) Inventors: Irving H. Zucker, Omaha, NE (US); Alicia Marie Schiller, Bellevue, NE (US); Peter Ricci Pellegrino, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 89 days.

(21) Appl. No.: 16/087,988

(22) PCT Filed: Mar. 22, 2017

(86) PCT No.: PCT/US2017/023557
§ 371 (c)(1),
(2) Date: Sep. 24, 2018

(87) PCT Pub. No.: WO2017/165500
PCT Pub. Date: Sep. 28, 2017

(65) Prior Publication Data
US 2019/0261866 A1    Aug. 29, 2019

Related U.S. Application Data

(60) Provisional application No. 62/312,513, filed on Mar. 24, 2016.

(51) Int. Cl.
*A61B 5/02* (2006.01)
*A61B 5/021* (2006.01)
(Continued)

(52) U.S. Cl.
CPC .......... *A61B 5/02007* (2013.01); *A61B 5/021* (2013.01); *A61B 5/201* (2013.01);
(Continued)

(58) Field of Classification Search
CPC ..... A61B 5/02007; A61B 5/021; A61B 5/201; A61B 5/726; A61B 5/742; A61B 5/7475; A61B 5/024; A61B 5/026
(Continued)

(56) References Cited

U.S. PATENT DOCUMENTS

| 5,417,220 A * | 5/1995 | Apple ................ A61B 5/02007 600/493 |
| 2005/0216199 A1* | 9/2005 | Banet ................... A61B 5/0022 702/19 |

(Continued)

OTHER PUBLICATIONS

Sheng Lu, Ki Hwan Ju, Chon KH. A new algorithm for linear and nonlinear ARMA model parameter estimation using affine geometry [and application to blood flow/pressure data]. IEEE Transactions on Biomedical Engineering (Year: 2001).*
(Continued)

*Primary Examiner* — William J Levicky
*Assistant Examiner* — Alexander M Eisenberg
(74) *Attorney, Agent, or Firm* — Fish & Richardson P.C.

(57) ABSTRACT

Sympathetic vasomotor identification and quantification systems that provide ways to assess therapies, diseases, and conditions which affect sympathetic innervation and function are described. Because sympathetic vasomotion relies on intact, functional sympathetic nerves, some embodiments of the sympathetic vasomotor identification and quantification systems described herein include a signal processing functionality that establishes sympathetic vasomotor signatures through the collection of arterial blood pressure and blood flow signals.

21 Claims, 8 Drawing Sheets

(51) Int. Cl.
A61B 5/20 (2006.01)
A61B 5/00 (2006.01)
A61B 5/024 (2006.01)

(52) U.S. Cl.
CPC .............. *A61B 5/726* (2013.01); *A61B 5/742* (2013.01); *A61B 5/7475* (2013.01); *A61B 5/024* (2013.01)

(58) Field of Classification Search
USPC ................................ 600/301, 481, 485, 504
See application file for complete search history.

(56) References Cited

U.S. PATENT DOCUMENTS

| | | | | |
|---|---|---|---|---|
| 2008/0021325 | A1* | 1/2008 | Drost | A61B 8/4227 600/454 |
| 2011/0071378 | A1* | 3/2011 | McKenna | A61B 5/6838 600/364 |
| 2014/0107437 | A1 | 4/2014 | Pinsky | |
| 2014/0187941 | A1* | 7/2014 | Shusterman | A61B 8/04 600/438 |
| 2014/0276746 | A1* | 9/2014 | Nabutovsky | A61B 5/4848 606/33 |
| 2014/0278285 | A1* | 9/2014 | Marmarelis | G16H 50/50 703/2 |

OTHER PUBLICATIONS

Extended European Search Report in EP Appln. No. 17771046, dated Dec. 3, 2018, 10 pages.
Kandzari et al, "Predictors of blood pressure responses in the SYMPLICITY HTN-3 trial," Eur Heart J. Jan. 21, 2015, pp. 219-227.
Mahfoud et al, "Renal denervation: symply trapped by complexity?" Euro Heart J. Jan. 21, 2015, pp. 199-202.
PCT International Search Report and Written Opinon in International Appln. No. PCT/US/2017/23557, dated Jun. 9, 2017, 12 pages.
Schiller et al, "Renal nerves dynamically regulate renal blood flow in conscious healthy rabbits," Am J. Physical Regul Integr Comp Physical, Nov. 4, 2015, pp. R156-R166.
Dibona et al., "Effect of renal denervation on dynamic autoregulation of renal blood flow," Am. J. Psych.: Renal Physiology, 2004, 286(6):F1209-F1218.
European Office Action in European Appln. No. 17771046.4, dated Jul. 22, 2020, 9 pages.

* cited by examiner

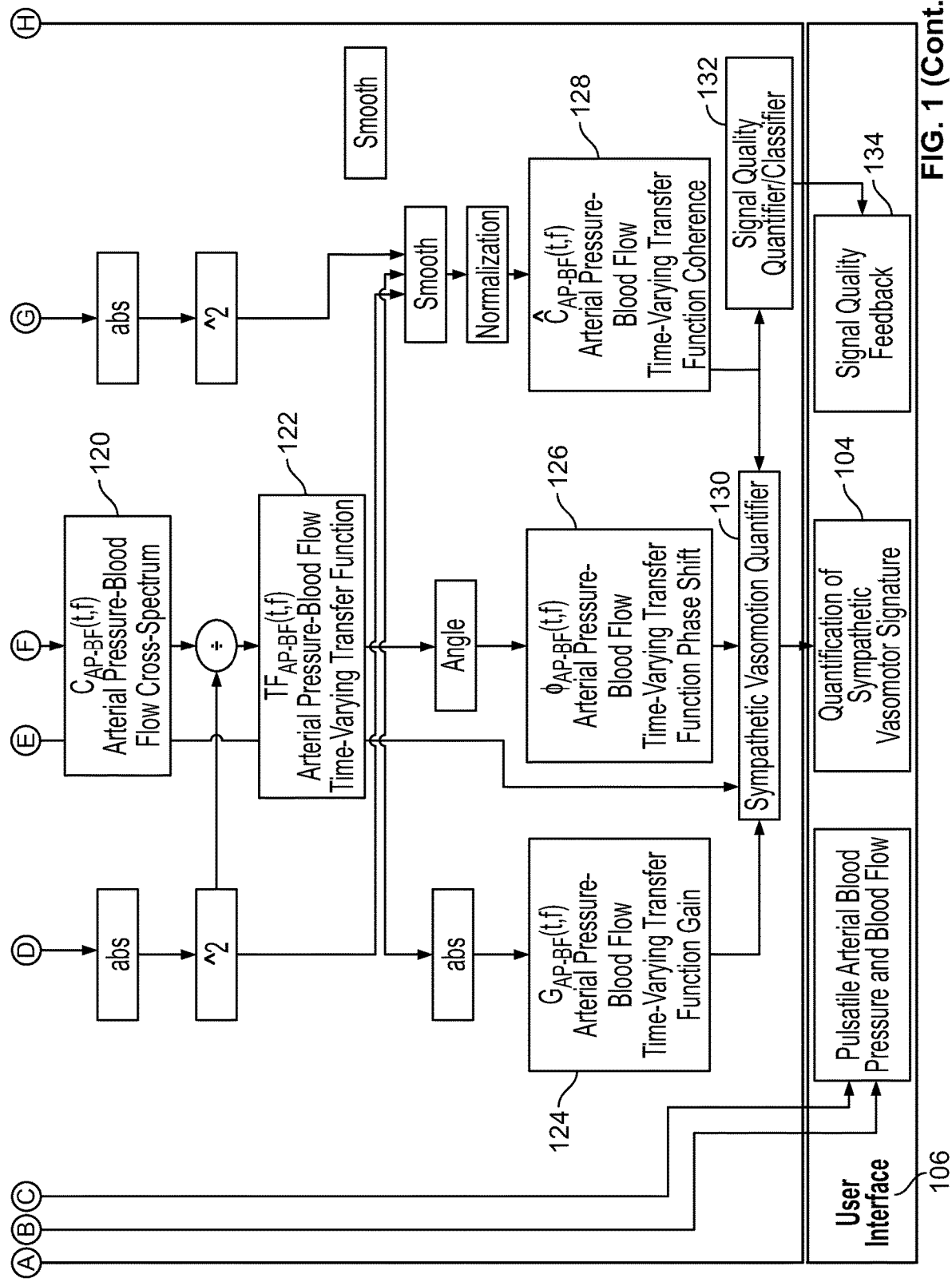

DEVICES AND METHODS FOR DETECTING AND MEASURING SYMPATHETIC VASOMOTION

CROSS REFERENCE TO RELATED APPLICATIONS

This application is a National Stage Application under 35 U.S.C. § 371 and claims the benefit of International Application No. PCT/US2017/023557, filed Mar. 22, 2017, which claims the benefit of U.S. Provisional Application No. 62/312,513, filed Mar. 24, 2016. The disclosure of the prior application is considered part of and is incorporated by reference in the disclosure of this application.

STATEMENT AS TO FEDERALLY SPONSORED RESEARCH

This invention was made with government support under Grant No. P01 HL062222 and Grant No. F30 HL118974 awarded by the National Institutes of Health. The government has certain rights in the invention.

TECHNICAL FIELD

The present disclosure relates to sympathetic vasomotor identification and quantification systems. The systems provide ways to assess therapies, diseases, and conditions which affect sympathetic innervation and function.

BACKGROUND

The sympathetic nervous system is an important guardian of body homeostasis that innervates arteries and veins releasing norepinephrine and causing these blood vessels to constrict. This norepinephrine release is rhythmic and leads to a rhythmic constriction and relaxation of the vessels that is known as sympathetic vasomotion.

SUMMARY

The present disclosure describes sympathetic vasomotor identification and quantification systems that provide ways to assess therapies, diseases, and conditions which affect sympathetic innervation and function. Because sympathetic vasomotion relies on intact, functional sympathetic nerves, systems described herein include a signal processing functionality that establishes sympathetic vasomotor signatures through the collection of arterial blood pressure and blood flow signals.

In one aspect, this disclosure is directed to a sympathetic vasomotion monitoring system that includes a user interface comprising a display, and a sympathetic vasomotion monitoring device comprising a sympathetic vasomotion quantifier. The sympathetic vasomotion monitoring device is configured to: (1) receive one or more blood pressure signals corresponding to a time-based series of blood pressure readings from a blood pressure monitoring device; (2) receive one or more blood flow signals corresponding to a time-based series of blood flow readings from a blood flow monitoring device; (3) calculate, by the sympathetic vasomotion quantifier, one or more quantifications of a sympathetic vasomotion signature based on: (a) the time-based series of blood pressure readings, (b) the time-based series of blood flow readings, and (c) a set of sympathetic vasomotion quantifier parameters comprising one or more types of physiological data; and (4) output to the display: (i) the one or more quantifications of the sympathetic vasomotion signature, (ii) the time-based series of blood pressure readings, (iii) the time-based series of blood flow readings, and (iv) a signal quality metric indicative of a quality of at least the one or more blood flow signals corresponding to the time-based series of blood flow readings.

Such a sympathetic vasomotion monitoring system may optionally include one or more of the following features. The set of sympathetic vasomotion quantifier parameters comprises blood pressure data and blood flow data may correspond to a specific vascular bed. The specific vascular bed may be a renal vascular bed. The set of sympathetic vasomotion quantifier parameters may include blood pressure data and blood flow data associated with a disease or condition. The disease or condition may be selected from a group consisting of: epilepsy, spinal-cord injuries, drug-induced autonomic dysfunction, pheochromocytoma, migraine, sleep apnea, adrenal insufficiency, mastocytosis, complex regional pain syndrome, chronic fatigue syndrome, alcoholism, carcinoid tumors, cancer, cyclic vomiting, neuroleptic malignant syndrome, hypertension, heart failure, cardiomyopathy, Takotsubo syndrome, chronic kidney failure, metabolic syndrome, insulin resistance, obesity, panic disorder, hemodynamic instability, hemorrhage, shock, and cerebrovascular accident. The set of sympathetic vasomotion quantifier parameters may include blood pressure data and blood flow data associated with a treatment. The treatment may be a renal denervation treatment. The one or more quantifications of the sympathetic vasomotion signature output to the display may include a sympathetic vasomotion quantifier comparing current sympathetic vasomotion to a healthy control. The one or more quantifications of the sympathetic vasomotion signature output to the display may include a sympathetic vasomotion quantifier comparing current sympathetic vasomotion to a patient's prior data.

In another aspect, this disclosure is directed to a method for monitoring sympathetic vasomotion. The method includes: (a) receiving at a sympathetic vasomotion monitoring device (i) one or more blood pressure signals corresponding to a time-based series of blood pressure readings from a blood pressure monitoring device and (ii) one or more blood flow signals corresponding to a time-based series of blood flow readings from a blood flow monitoring device; (b) calculating, by a processor of the sympathetic vasomotion monitoring device, an arterial pressure-blood flow time-varying transfer function; (c) calculating, by a sympathetic vasomotion quantifier of the sympathetic vasomotion monitoring device, one or more quantifications of a sympathetic vasomotion signature based on the arterial pressure-blood flow time-varying transfer function and a set of sympathetic vasomotion quantifier parameters comprising one or more types of physiological data; (d) outputting, to a display, the one or more quantifications of the sympathetic vasomotion signature; and (e) displaying, at the display, the one or more quantifications of the sympathetic vasomotion signature.

Such a method for monitoring sympathetic vasomotion may optionally include one or more of the following features. The set of sympathetic vasomotion quantifier parameters may include blood pressure data and blood flow data corresponding to a specific vascular bed. The specific vascular bed may be a renal vascular bed. The set of sympathetic vasomotion quantifier parameters may include blood pressure data and blood flow data associated with a disease or condition. The disease or condition may be selected from a group consisting of: epilepsy, spinal-cord injuries, drug-induced autonomic dysfunction, pheochromocytoma, migraine, sleep apnea, adrenal insufficiency, mastocytosis, complex regional pain syndrome, chronic fatigue syndrome, alcoholism, carcinoid tumors, cancer, cyclic vomiting, neuroleptic malignant syndrome, hypertension, heart failure, cardiomyopathy, Takotsubo syndrome, chronic kidney failure, metabolic syndrome, insulin resistance, obesity, panic disorder, hemodynamic instability, hemorrhage, shock, and cerebrovascular accident. The set of sympathetic vasomotion quantifier parameters may include blood pressure data and blood flow data associated with a treatment. The treatment may be a renal denervation treatment. The displaying the one or more quantifications of the sympathetic vasomotion signature may include displaying a comparison between current sympathetic vasomotion and a healthy control. The displaying the one or more quantifications of the sympathetic vasomotion signature may include displaying a comparison between current sympathetic vasomotion and a patient's prior data. The method may also include determining a treatment protocol based on the displayed one or more quantifications of the sympathetic vasomotion signature. The treatment protocol may include a treatment time for a renal denervation procedure.

In another aspect, this disclosure is directed to a sympathetic vasomotion monitoring system that includes a user interface comprising a display, and a sympathetic vasomotion monitoring device comprising a sympathetic vasomotion quantifier. The sympathetic vasomotion monitoring device may be configured to: (i) receive one or more blood pressure signals corresponding to a time-based series of blood pressure readings; (ii) receive one or more blood flow signals corresponding to a time-based series of blood flow readings; (iii) calculate, by the sympathetic vasomotion quantifier, one or more quantifications of a sympathetic vasomotion signature based on: (a) the time-based series of blood pressure readings, (b) the time-based series of blood flow readings, and (c) a set of sympathetic vasomotion quantifier parameters comprising physiological data; and (iv) output to the display the one or more quantifications of the sympathetic vasomotion signature.

Certain embodiments described herein may have particular advantages. For example, some embodiments of the sympathetic vasomotor identification and quantification systems can provide real-time, reliable, and quantitative indications of sympathetic vasomotion. Accordingly, in some embodiments the technology can help diagnose the presence of sympathetic failure and sympathetically-mediated pain, characterize the extent of sympathetic failure, differentiate between types of sympathetic failure, and/or stratify patients within one disease type to personalize treatment options and assess the response to therapy. The systems also allow for sympathetic vasomotion to be measured regionally and/or locally, such as in a particular vascular bed.

Additionally, in some embodiments the sympathetic vasomotor identification and quantification systems described herein are advantageously non-invasive, using arterial blood flow and blood pressure signals to calculate the quantitative sympathetic vasomotion readout.

Furthermore, in some embodiments the sympathetic vasomotor identification and quantification systems described herein enable continuous, real-time monitoring of sympathetic vasomotion. As such, the sympathetic vasomotor identification and quantification systems can be advantageously used in parallel with many treatments (such as, but not limited to, renal denervation), while providing a real-time readout as to whether the treatment is effective.

Other features and advantages of the invention will be apparent from the following detailed description and figures, and from the claims.

DETAILED DESCRIPTION

Figure 1:
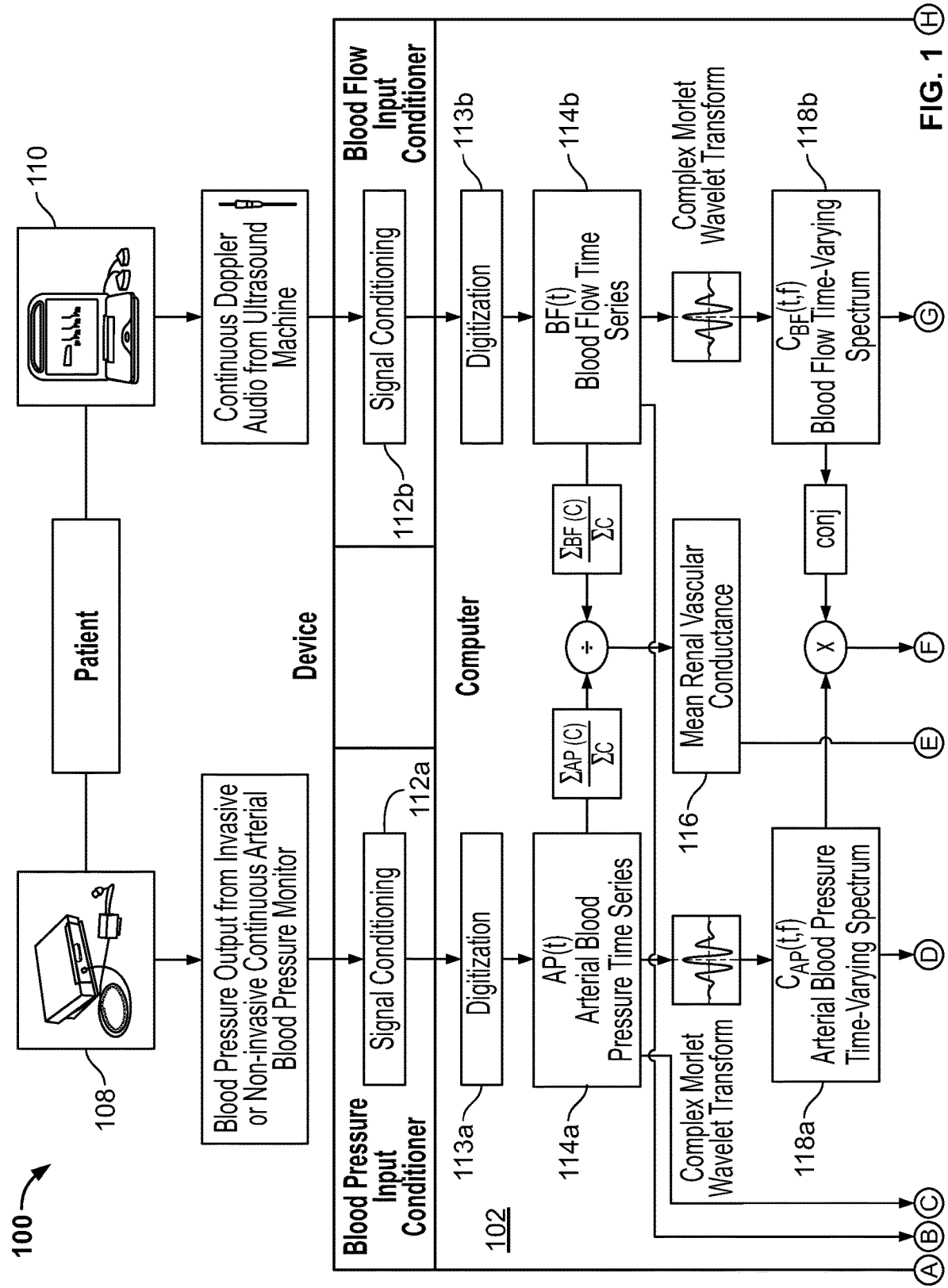
FIG. 1 is a block diagram that depicts the structure of an example sympathetic vasomotion identification and quantification system, in accordance with some embodiments.

Turning to the figures, FIG. 1 is a block diagram depicting the structure of an example sympathetic vasomotion identification and quantification system 100 in accordance with some embodiments provided herein. In the depicted embodiment, the sympathetic vasomotion identification and quantification system 100 includes a sympathetic vasomotion monitoring device 102 for quantifying sympathetic vasomotion. The sympathetic vasomotion monitoring device 102 outputs a quantification of a sympathetic vasomotion signature 104 to be displayed via a user interface 106.

In the depicted embodiment, the sympathetic vasomotion identification and quantification system 100 also includes an arterial blood pressure monitor 108 and an arterial blood flow monitor 110. The arterial blood pressure monitor 108 and the arterial blood flow monitor 110 provide signals corresponding to a patient's arterial blood pressure and arterial blood flow, respectively, to the sympathetic vasomotion monitoring device 102.

In some cases, the arterial blood pressure signal may be acquired using non-invasive methods such as, but not limited to, oscillometry, tonometry, volume-clamp, pulse wave velocity, and pulse transit time method. In some cases, the arterial blood pressure signal may be acquired more invasively using methods such as, but not limited to, by placement of an arterial pressure transducer directly in a subject's artery. In some cases, the blood flow signal may be acquired as blood flow velocity using techniques such as, but not limited to, ultrasound or laser Doppler technology, or by transit-time ultrasound.

While in the depicted embodiment the arterial blood pressure monitor 108 and the arterial blood flow monitor 110 are depicted as separate monitoring systems, in some embodiments the arterial blood pressure and the blood flow signals are obtained from a combined system. For example, in some embodiments signals corresponding to a patient's arterial blood pressure and blood flow can be obtained from an intravascular device that includes a pressure sensor and a flow sensor that are combined on the same wire or catheter. In some embodiments, such a combined pressure/flow measuring device can be steerable and may include additional advantageous functionalities. Some non-limiting examples of such combination pressure/flow measuring devices are the COMBOWIRE® XT pressure/flow guide wires marketed by Volcano Corporation of San Diego, Calif., USA.

In the depicted embodiment of sympathetic vasomotion identification and quantification system 100, the signals output from the arterial blood pressure monitor 108 and the arterial blood flow monitor 110 are conditioned by signal conditioners represented here by signal conditioning 112a and 112b, which are described further below in reference to FIG. 2. After signal conditioning 112a and 112b, the resulting signals are digitized at signal digitization 113a and 113b. Thereafter, the digitized signals are turned into an arterial blood pressure time series 114a and an arterial blood flow time series 114b respectively.

In the depicted embodiment, the arterial blood pressure time series 114a and the arterial blood flow time series 114b are used to calculate a mean vascular conductance 116. The mean vascular conductance 116 gives a snapshot of the static vascular behavior of the patient. In some embodiments, the arterial blood pressure time series 114a and the arterial blood flow time series 114b are transformed into an arterial blood pressure time-varying spectrum 118a and an arterial blood flow time-varying spectrum 118b, respectively, using complex Morlet Wavelet transforms or other time-frequency (e.g., Gabor transform) or time-scale (complex Gaussian wavelet) transforms.

Still referring to FIG. 1, in the depicted embodiment the arterial blood pressure time-varying spectrum 118a and the arterial blood flow time-varying spectrum 118b are used to calculate an arterial pressure-blood flow cross-spectrum 120 and an arterial pressure-blood flow time-varying transfer function 122. The gain 124, phase shift 126, and coherence 128 of the arterial pressure-blood flow time-varying transfer function 122 are calculated and input to a sympathetic vasomotion quantifier 130 alongside the mean renal vascular coherence 116. The coherence 128 of the arterial pressure-blood flow time-varying transfer function 122 is also provided to a signal quality quantifier 132.

In some embodiments, the signal quality quantifier 132 processes the coherence 128 to quantify and/or classify the quality of one or more of the signal(s). For example, in some embodiments the signal quality quantifier 132 can output a value such as a percentage or other scaled numeric value (e.g., zero to ten) as an expression of the quality of the signal. In another example, the quantifier can output one or more indicia such as a rating (e.g., an "A" to "F" letter grade, a zero to five-star rating, and the like), a class (e.g., "great," "good," "OK," "poor," etc.), or any other appropriate form of classification of a signal's quality. In some embodiments, the output of the quantifier 132 is output as a signal quality feedback value 134 to the user interface 106.

The sympathetic vasomotion quantifier 130 is application specific, meaning that sympathetic vasomotion quantifier parameters (i.e., one or more types of physiological data) of the sympathetic vasomotion quantifier 130 differ depending on which vascular bed is being monitored and/or which disease or treatment is being monitored. The particular sympathetic vasomotion quantifier 130 that is used in the sympathetic vasomotion monitoring device 102 for a particular monitoring period may be selected by a clinician or other user of the sympathetic vasomotion identification and quantification system 100.

In the depicted embodiment, the sympathetic vasomotion quantifier 130 leverages both the frequency and the magnitude of the gain and phase time-frequency distributions to identify that the vasomotion is of sympathetic origin. Ohm's Law assures a constant, linear relationship between blood pressure and blood flow for passive blood vessels, and thus active, time-varying vasomotion can be identified and quantified by the time variability in the pressure-flow relationship. This time variability manifests directly as low coherence as well as elevated measures of variability (standard deviation, interquartile range) of the pressure-flow relationship over time.

In frequency, sympathetic vasomotion can affect the pressure-flow relationship at higher frequencies than other sources of vasomotion. For example, in rabbit studies, the pressure-flow relationship is affected at high frequencies of between 0.2 and 0.75 Hz. In humans, this high frequency is approximately 0.1 Hz. Other sources of vasomotion, for example auto-regulatory mechanisms in the kidney, occur at lower frequencies, allowing them to be filtered out. For example, the auto-regulator mechanisms in a rabbit kidney produce affects to the pressure-flow relationship at frequencies of 0.02-0.2 Hz. In gain, sympathetic vasomotion, as a vasoconstrictor, decreases the magnitude of the pressure-flow admittance. In phase, sympathetic vasomotion is readily distinguishable from autoregulatory mechanisms, as autoregulatory mechanisms lag changes in renal blood flow (i.e., give rise to time-frequency distributions with positive phase) whereas sympathetic vasomotion gives rise to pressure-flow variability centered either at zero or at a negative phase lag, depending on the vascular bed and hemodynamic state. The occurrence of high-frequency, low-gain, negative-phase, low-coherence occurrences of the pressure-flow relationship can be used to sensitively and specifically identify as well as quantify sympathetic vasomotion in a vascular bed of interest.

In some embodiments, the sympathetic vasomotion quantifier 130 may look at a particular portion of the time-varying data (for example a one, two, three, four, five, six, seven, eight, nine, or ten-minute period, or longer), and compare the gain, phase shift, and coherence across that portion to a control data set or a previously-taken data set from the same patient. Depending on the disease, condition, or treatment being monitored, the sympathetic vasomotion quantifier 130 may be provided with and/or utilize a different control data set. For example, if a renal denervation treatment is being monitored, the sympathetic vasomotion quantifier 130 may compare the time-varying data with a data from a denervated kidney and provide a quantification of a sympathetic vasomotor signature 104 to the user interface 106 based on the comparison performed by the sympathetic vasomotion quantifier 130.

In some embodiments, the sympathetic vasomotion identification and quantification system 100 can assess sympathetic activity in diseases where excessive sympathetic activity contributes to disease progression and mortality. For example, such diseases can include, but are not limited to, cardiovascular diseases like hypertension, heart failure, cardiomyopathy, Takotsubo syndrome, renal diseases like chronic kidney failure, metabolic diseases like metabolic syndrome, insulin resistance, and obesity, and psychiatric diseases like panic disorder.

In some embodiments, the sympathetic vasomotion identification and quantification system 100 can help diagnose the presence of sympathetic failure and sympathetically-mediated pain, characterize the extent of sympathetic failure, differentiate between types of sympathetic failure, and stratify patients within one disease to personalize treatment options and assess the response to therapy. In some embodiments, the system 100 and method can be used for patients with primary disorders of the autonomic nervous system, including, but not limited to, postural tachycardia syndrome (POTS), neurogenic orthostatic hypotension, vasovagal syncope, pure autonomic failure, autonomic epilepsy, neutrally-mediated syncope (NMS, formerly called neurocardiogenic syncope or neutrally-mediated hypotension), multiple system atrophy (Shy-Drager Syndrome), cerebral salt-wasting syndrome, deficiencies of tetrahydrobioperterin, tyrosine hydroxylase oraromatic L-amino acid decarboxylase, dopamine beta-hydroxylase deficiency, Menkes disease and other ATP7A-related disorders, norepinephrine transporter deficiency, monoamine oxidase deficiency, and congenital central hypoventilation syndrome and other PHOX2B-related disorders.

In some embodiments, the sympathetic vasomotion identification and quantification system 100 can be used for peripheral autonomic disorders including, but not limited to, diabetic autonomic dysfunction, amyloidotic autonomic failure, autoimmune autonomic ganglionopathy, Guillain-Barre' syndrome, hereditary autonomic neuropathies, familial dysautonomia (i.e. Riley-Day Syndrome), and vitamin B12 deficiency. In some embodiments, the sympathetic vasomotion identification and quantification system 100 can be used for patients with other chronic, progressive diseases involving the sympathetic nervous system including, but not limited to, Parkinson's disease, dementia with Lewy Bodies, and pure autonomic failure that result in sympathetic failure. Further, in some embodiments the sympathetic vasomotion identification and quantification system 100 can be used in the evaluation of patients presenting with complaints that frequently have autonomic components, including, but not limited to, syncope, orthostatic intolerance, impotence (male erectile dysfunction), hyper- and hypo-hydrosis, sleep apnea, and fecal incontinence. Moreover, in some embodiments the sympathetic vasomotion identification and quantification system 100 can be used for patients diagnosed with conditions which may have autonomic involvement, such as epilepsy, spinal-cord injuries, drug-induced autonomic dysfunction, pheochromocytoma, migraine, sleep apnea, adrenal insufficiency, mastocytosis, complex regional pain syndrome, chronic fatigue syndrome, alcoholism, carcinoid tumors, cancer (which can cause paraneoplastic autonomic dysfunction), cyclic vomiting, and neuroleptic malignant syndrome.

Figure 2A:
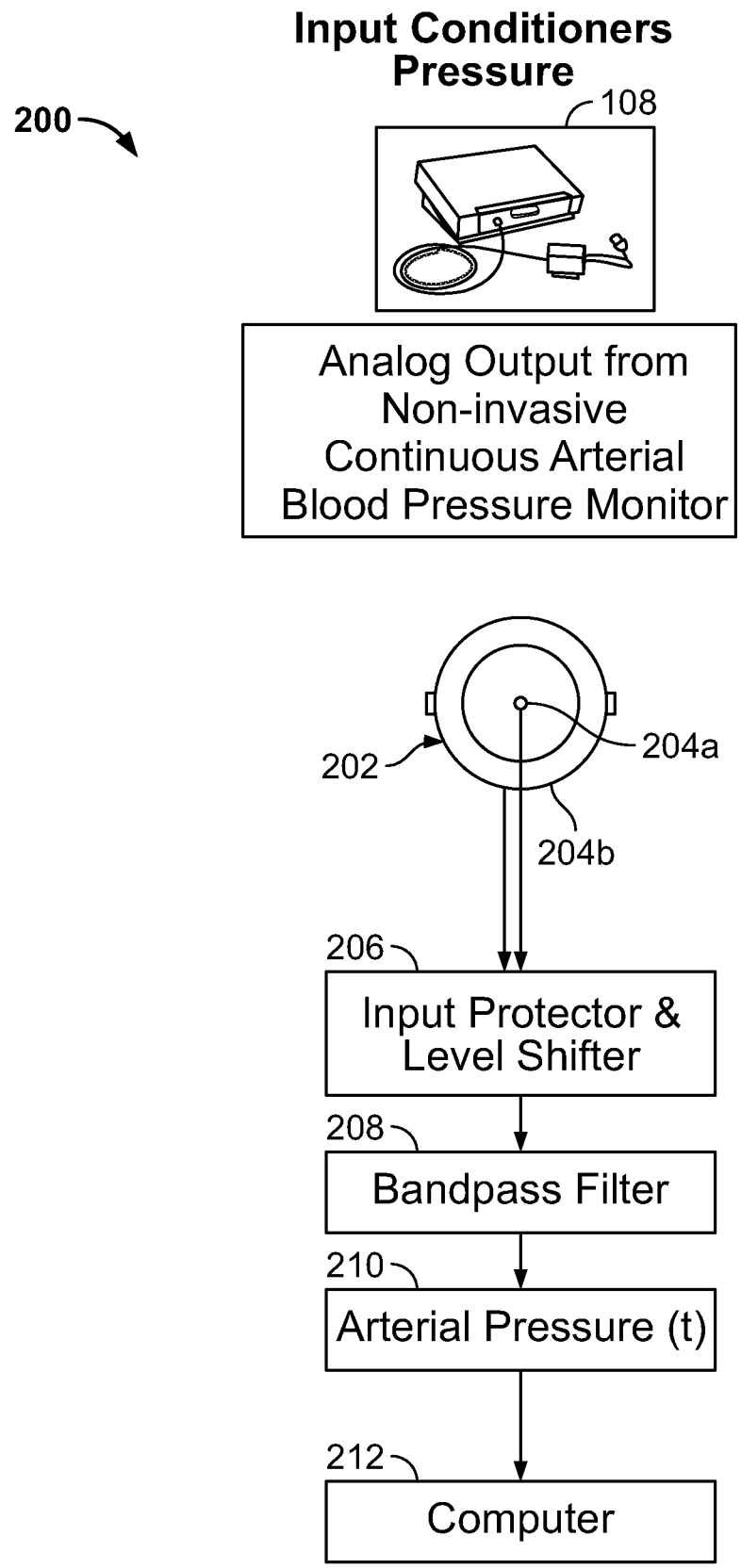
FIG. 2A is a block diagram of an example blood pressure input conditioner.

FIG. 2A is a block diagram of an example blood pressure input signal conditioner 200. In general, in some embodiments the blood pressure input signal conditioner 200 accepts an analog electrical output signal from a non-invasive, continuous arterial blood pressure monitor, and prepares the signal for digitization. In some embodiments, the blood pressure input signal conditioner 200 can perform the signal conditioning 112a of FIG. 1. For example, the blood pressure input signal conditioner 200 can be used to interface the example arterial blood pressure monitor 108 in preparation for the digitization 113a of FIG. 1.

A connector 202 includes a blood pressure signal contact 204a and a ground contact 204b. In some embodiments, the connector 202 can be configured to electrically interface with a blood pressure monitor. For example, the connector 202 can be formed as part of a jack that plugs into the arterial blood pressure monitor 108 to receive analog electrical waveforms that are representative of blood pressure readings.

In the depicted embodiment, the blood pressure signal contact 204a and the ground contact 204b are in electrical communication with an input protector and level shifter 206. The input protector and level shifter 206, as the name suggests, performs at least two functions. First, the input protector and level shifter 206 includes circuitry that can resist the effects of voltages and/or currents present at the blood pressure signal contact 204a and the ground contact 204b. For example, the input protector and level shifter 206 can include circuitry that resists reverse polarities (e.g., a ground applied to the blood pressure signal contact 204a and/or a voltage applied to the ground contact 204b), resists electrical spikes (e.g., static shock), resists or snubs overvoltages (e.g., due to plugging the connector 202 into an incompatible device), or can help protect the device 100 from combinations of these and/or other non-blood pressure signal related electrical conditions. Second, the input protector and level shifter 206 includes circuitry that can provide electrical signal level shifting. For example, the input protector and level shifter 206 can be configured to amplify, attenuate, compress, expand, offset (e.g., combine a positive or negative DC voltage onto the blood pressure signal), or perform combinations of these and other appropriate forms of electrical signal modifications. The output of the input protector and level shifter 206 is a protected and modified signal based on the analog electrical waveforms received by the input protector and level shifter 206.

In the depicted embodiment, the input protector and level shifter 206 is in electrical contact with a signal filter 208, and passes the modified signal to the signal filter 208. The signal filter 208 performs frequency-based filtering of the modified signal and provides a filtered signal as an output. For example, the signal filter 208 may attenuate signal components in the modified signal that are above a predetermined frequency (e.g., low-pass filtering), below a predetermined frequency (e.g., high-pass filtering), between two predetermined frequencies (e.g., bandpass filtering), or are outside the range of two predetermined frequencies (e.g., notch filtering).

The output of the signal filter 208 is a filtered form of the blood pressure signal as modified by the input protector and level shifter 206. This resulting signal is provided as an arterial pressure signal 210. In some implementations, the arterial pressure signal 210 can be an analog waveform representative of the time-domain, protected, shifted, and filtered blood pressure signal received from the arterial blood pressure monitor 108.

In the depicted embodiment, the arterial pressure signal 210 is then provided to a computer 212. In some embodiments, the computer 212 can be or can comprise a portion of the sympathetic vasomotion monitoring device 102 (FIG. 1). For example, in some embodiments the arterial pressure signal 210 can be provided for digitization by the example digitization step 113a.

In some embodiments, the arterial blood pressure monitor 108 (FIG. 1) may be configured to provide digital signals that are representative of blood pressure readings, and the input protector and level shifter 206 and the filter 208 can include circuitry and/or software modules that when executed by a processor can protect, limit, and/or shift digital waveforms in order to provide a digital version of the arterial pressure signal 210. In some embodiments, such a digital version of the arterial pressure signal 210 may be provided directly to the sympathetic vasomotion monitoring device 102 as the example arterial blood pressure time series 114a.

Figure 2B:
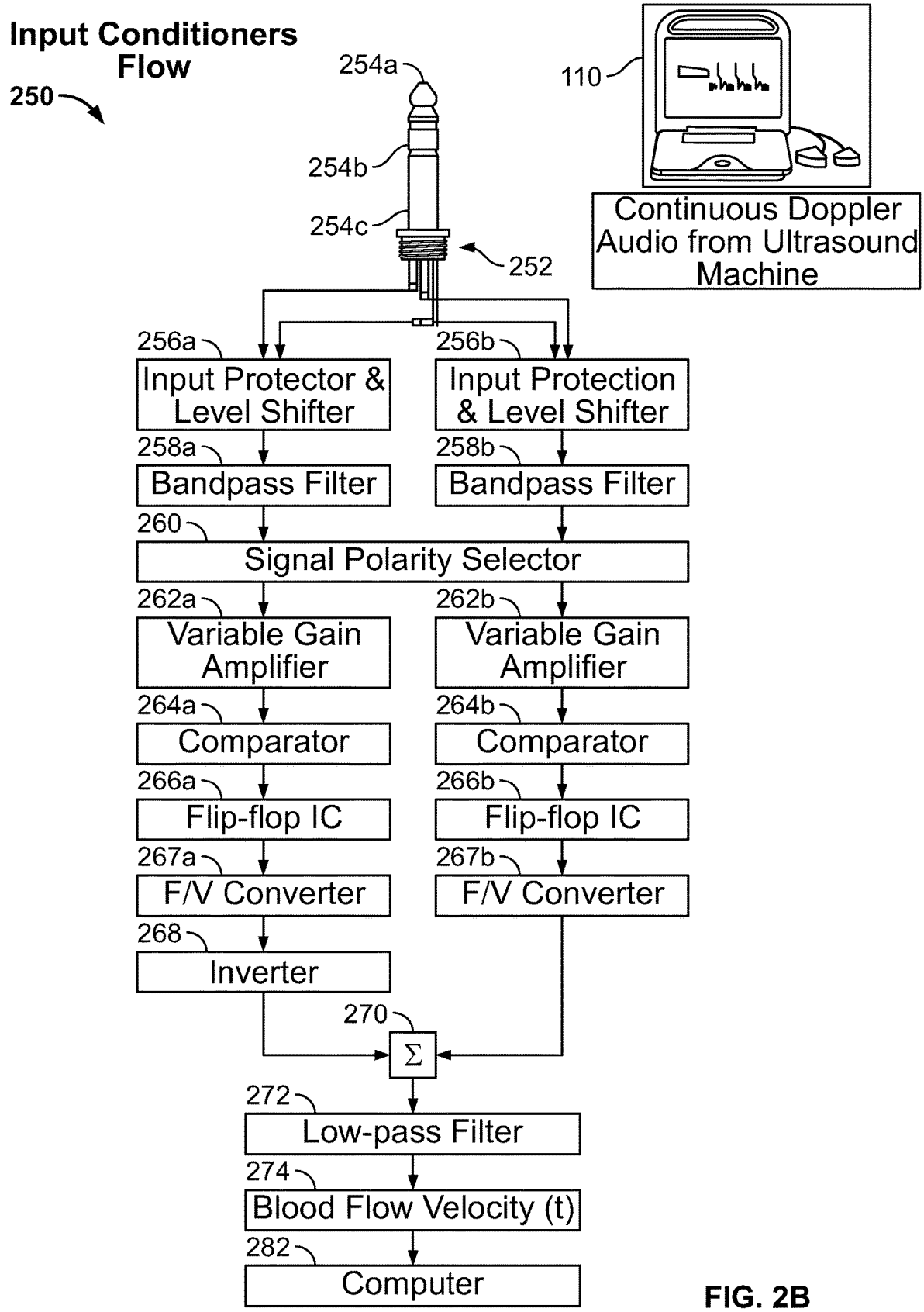
FIG. 2B is a block diagram of an example blood flow input conditioner.

FIG. 2B is a block diagram of an example blood flow input signal conditioner 250. In general, in the depicted embodiment the blood flow input signal conditioner 202 accepts an analog electrical output signal that represents the continuous Doppler audio from a non-invasive, ultrasound machine, and prepares the signal for digitization. In some embodiments, the blood flow input signal conditioner 250 can perform the signal conditioning 112b of FIG. 1. For example, the blood flow input signal conditioner 250 can be used to interface the example arterial blood flow monitor 110 in preparation for the digitization 113b of FIG. 1.

A connector 252 includes a blood flow signal contact 254a, a blood flow signal contact 254b, and a ground contact 254c. In some embodiments, the connector 202 can be configured to electrically interface with a blood pressure monitor. For example, the connector 252 can be formed as part of a jack that plugs into the arterial blood flow-monitor 110 to receive analog electrical, waveforms that are representative of blood flow readings.

In the depicted embodiment, the blood pressure signal contact 254a and the ground contact 254c are in electrical communication with an input protector and level shifter 256a. In some embodiments, the input protector and level shifter 256a, as the name suggests, performs at least two functions. First, the input protector and level shifter 256a includes circuitry that can resist the effects of voltages and/or currents present at the blood pressure signal contact 254a and the ground contact 254c. For example, the input protector and level shifter 256a can include circuitry that resists reverse polarities (e.g., a ground applied to the blood flow signal contact 254a and/or a voltage applied to the ground contact 254c), resists electrical spikes (e.g., static shock), resists or snubs over-voltages (e.g., due to plugging the connector 252 into an incompatible device), or can help protect the device 100 from combinations of these or other non-blood pressure signal related electrical conditions. Second, the input protector and level shifter 256a includes circuitry that can provide electrical signal level shifting. For example, the input protector and level shifter 256a can be configured to amplify, attenuate, compress, expand, offset (e.g., combine a positive or negative DC voltage onto the blood pressure signal), or perform combinations of these and other appropriate forms of electrical signal modifications. The output of the input protector and level shifter 256a is a protected and modified signal based on the analog electrical waveforms received by the input protector and level shifter 256a.

In the depicted embodiment, the blood pressure signal contact 254b and the ground contact 254c are in electrical communication with an input protector and level shifter 256b. The input protector and level shifter 256b performs substantially the same functions for the signals provided at the blood pressure signal contact 254b and the ground contact 254c as the input protector and level shifter 256a performs for the signals provided at the blood pressure signal contact 254a and the ground contact 254c. The output of the input protector and level shifter 256b is a protected and modified signal based on the analog electrical waveforms received by the input protector and level shifter 256b.

In the depicted embodiment, the input protector and level shifter 256a is in electrical contact with a signal filter 258a, and passes the modified signal to the signal filter 258a. The signal filter 258a performs frequency-based filtering of the modified signal and provides a filtered signal as an output. For example, the signal filter 258a may attenuate signal components in the modified signal that are above a predetermined frequency (e.g., low-pass filtering), below a predetermined frequency (e.g., high-pass filtering), between two predetermined frequencies (e.g., bandpass filtering), or are outside the range of two predetermined frequencies (e.g., notch filtering).

In the depicted embodiment, the input protector and level shifter 256b is in electrical contact with a signal filter 258b, and passes modified signal to the signal filter 258b. The signal filter 258b performs substantially the same function for the modified signal of the input protector and level shifter 256b as the signal filter 258a performs for the for the modified signal of the input protector and level shifter 256a.

The output of the signal filters 258a and 258b are filtered forms of the blood flow signals as modified by the input protector and level shifters 256a and 256b. These resulting signals are provided to a signal polarity selector 260.

In general, one of the blood flow signals will be a positive signal, and the other will be a negative signal. However, in some implementations these signals may be received with reversed polarity (e.g., the connector 252 was plugged in backwards, the ultrasound machine was misconfigured or used in error). As such, in some such implementations, the polarity of the signals may need to be reversed before they can be properly conditioned and/or processed further.

In some embodiments, the signal polarity selector 260 includes circuitry that identifies the polarity of the blood flow signals as provided by the signal filters 258a and 258b and a switching network that can direct the blood flow signals to a pair of outputs based on the identified polarity (e.g., reverse the polarity of the signals). For example, the signal polarity selector 260 can determine if the output of the signal filter 258a should be provided to a variable gain amplifier 262a and the output of the signal filter 258b should be provided to a variable gain amplifier 262b, or if the polarity should be reversed by providing the output of the signal filter 258a the variable gain amplifier 262b and by providing the output of the signal filter 258b to the variable gain amplifier 262a.

In the depicted embodiment, the variable gain amplifiers 262a and 262b are configured to provide a predetermined amount of gain or attenuation to the signals provided by the signal polarity selector 260. In some implementations, the variable gain amplifiers 262a and 262b may amplify or attenuate the two received signals differently (e.g., to increase the balance between waveforms).

In the depicted embodiment, the variable gain amplifier 262a provides an amplified signal to a comparator 264a. The comparator 264a compares the amplified signal to a predetermined comparison voltage, and provides one or more digital signals that indicate which of the amplified signal or the comparison voltage is higher. The one or more digital signals is/are provided to a flip-flop 266a. The variable gain amplifier 262b provides an amplified signal to a comparator 264b that performs a substantially similar function as the comparator 264a, and the resulting digital signal is provided to a flip-flop 266b.

In the depicted embodiment, the flip-flop 266a provides a toggled digital output that is in one of two stable states. The state of the toggled digital output is changed based on the digital signal received from the comparator 264a. The flip-flop 266a is configured to change its toggled digital output on and off in response to the received digital signal changing to a selected one of "off" or "on." For example, when the flip-flop 266a receives an "on" signal, the state of the toggled digital output can be toggled "on" or "off." The flip-flop 266b performs a substantially similar function as the flip-flop 266a, and provides a toggled digital output based on the digital signal received from the comparator 264b.

In the depicted embodiment, the toggled digital output of the flip-flop 266a is provided to a frequency-to-voltage converter 267a. The toggled digital output of the flip-flop 266b is provided to a frequency-to-voltage converter 267b. The voltage output of the frequency-to-voltage converter 267a, the blood flow velocity toward the ultrasound transducer, is passed to an inverter 268. The inverter 268 inverts this directional blood flow velocity so that it may be passed along with the output of the frequency-to-voltage converter 267*b* to a summing amplifier 270. The output of the summing amplifier 270 then represents the net blood arterial blood flow at a given point in time.

In the depicted embodiment, the combined digital output signal of the combiner 270 is provided to a signal filter 272. The signal filter 272 performs frequency-based filtering of the modified signal and provides a filtered signal as an output. For example, the signal filter 272 may attenuate signal components in the modified signal that are above a predetermined frequency (e.g., low-pass filtering), below a predetermined frequency (e.g., high-pass filtering), between two predetermined frequencies (e.g., bandpass filtering), or are outside the range of two predetermined frequencies (e.g., notch filtering).

The output of the signal filter 272 is a filtered form of the combined digital output signal provided by the combiner 270. This resulting signal is provided as blood flow velocity signal 274. In some implementations, the blood flow velocity signal 274 can be a digital waveform representative of the time-domain, protected, filtered, digitized, and combined blood flow signals received from the arterial blood flow monitor 110. In other embodiments, the arterial blood flow monitor could use a different method to measure blood flow, including, but not limited to, transit-time volumetric flow (e.g., from a peri-arterial probe) or intravascular Doppler flow velocity (e.g., from an intra-arterial catheter).

The blood flow velocity signal 274 is then provided to a computer 282. In some embodiments, the computer 212 can be or can comprise a portion of the sympathetic vasomotion monitoring device 102 (FIG. 1). For example, the blood flow velocity signal 274 can be provided for digitization by the example digitization step 113*b*.

In some embodiments, the arterial blood flow monitor 110 may be configured to provide digital signals that are representative of blood flow readings, and the input protector and components of the blood flow input signal conditioner 250 can include circuitry and/or software modules that when executed by a processor can protect, limit, shift, filter, repolarize, amplify, compare, toggle, and/or combine digital waveforms in order to provide a digital version of the blood flow velocity signal 274, which may be provided directly to the sympathetic vasomotion monitoring device 102 (FIG. 1) as the example arterial blood flow time series 114*b*.

Figure 3:
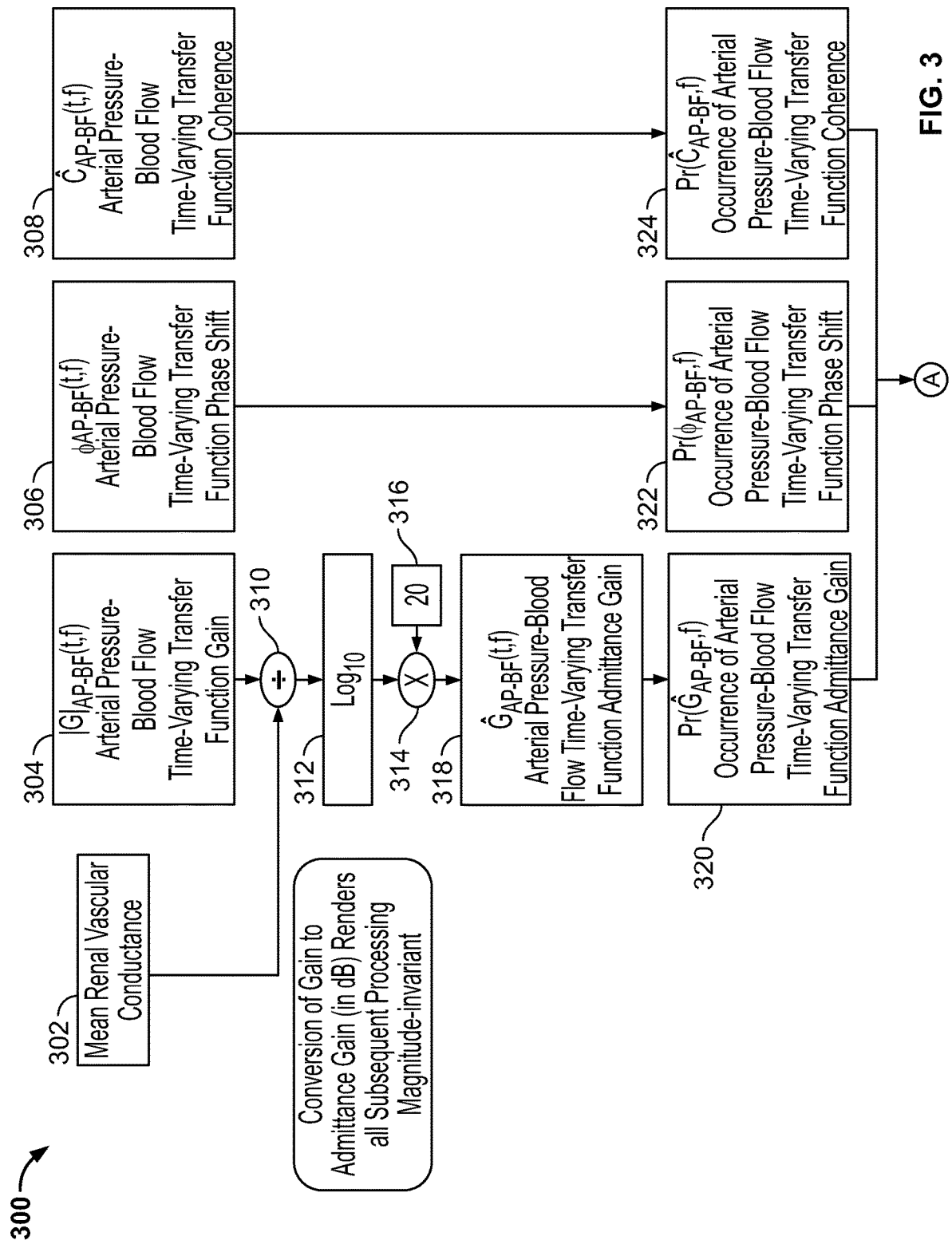
FIG. 3 is a flowchart depicting an example process for quantifying sympathetic vasomotion.
Figure 3:
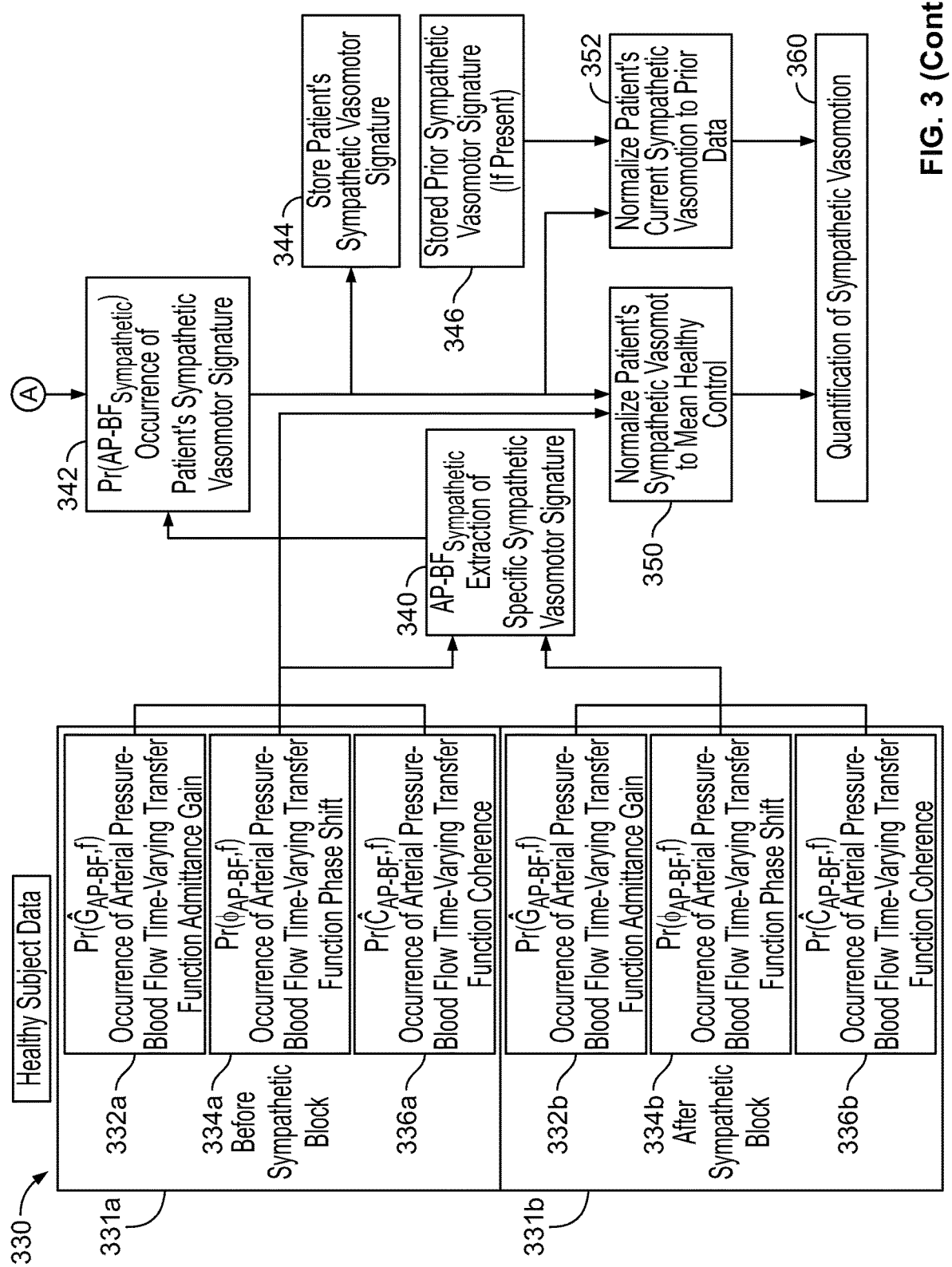

FIG. 3 is a flowchart depicting an example process 300 for quantifying the amount of renal sympathetic vasomotion occurring over time. In some implementations, the process 300 can be performed by the example sympathetic vasomotion quantifier 130 of FIG. 1.

In the process 300, a value 302 representative of a mean renal vascular conductance (e.g., the mean renal vascular conductance 116), a value 304 representative of an arterial pressure blood flow time-varying transfer function gain (e.g., gain 124), a value 306 representative of an arterial pressure blood flow time varying transfer function phase shift (e.g., phase shift 126), and a value 308 representative of an arterial pressure blood flow time-varying transfer function (e.g., coherence 128) are received.

The value 304 is divided (i.e., normalized) by value 302 in process 310 and converted 312 to a log 10 scale and multiplied 314 by a factor of twenty 316 to yield value 318, the admittance gain in dB. The conversion of gain to the admittance gain (in dB) can cause subsequent processing to be substantially magnitude-invariant. These admittance gain values 318 are calculated for the duration of the sympathetic vasomotion assessment, and this is then binned (e.g., into bins of 5 dB width) to yield the occurrence of admittance gain over the time course of the renal sympathetic vasomotion assessment, value 320.

The value 306 is calculated for the duration of the sympathetic vasomotion assessment, and these values are then binned (e.g., into bins of $\pi/10$ width) to yield the occurrence of phase shift over the time course of the renal sympathetic vasomotion assessment, value 322. The value 308 is calculated for the duration of the renal sympathetic vasomotion assessment, and these values are then binned (e.g., into bins of 0.05 width) to yield the occurrence of coherence over the time course of the renal sympathetic vasomotion assessment, value 322. The value 308 is applied to an occurrence of arterial pressure blood flow time-varying coherence transfer function to determine a value 324.

At this point in the example process 300, the blood pressure-blood flow relationship over time has been characterized in terms of the occurrence of admittance gain, phase shift, and coherence, and now the sympathetic vasomotion component of this relationship must be extracted and quantified. Identifying the sympathetic vasomotion signature is depicted in this example process 300 by using normative data from healthy subjects before and after sympathetic block. A collection 330 of healthy subject (e.g., patent) data is obtained in accordance with some embodiments of process 300. The collection can include a block of data 331*a* and a block of data 331*b*. The block of data 331*a* includes an occurrence of arterial pressure blood flow time-varying transfer function admittance gain value 332*a*, an occurrence of arterial pressure blood flow time-varying phase shift value 334*a*, and an occurrence of arterial pressure blood flow time-varying coherence value 336*a*. The values 332*a*, 334*a*, and 336*a* are values obtained before a sympathetic block has been performed (e.g., baseline "before" readings). The block of data 331*b* includes an occurrence of arterial pressure blood flow time-varying transfer function admittance gain value 332*b*, an occurrence of arterial pressure blood flow time-varying phase shift value 334*b*, and an occurrence of arterial pressure blood flow time-varying coherence value 336*b*. The values 332*b*, 334*b*, and 336*b* are values obtained after a sympathetic block has been performed (e.g., "after" readings).

The blood pressure-blood flow admittance gain, phase shift, and coherence occurrence that is significantly reduced by sympathetic blockade is sympathetic vasomotion. The occurrence bins that are affected in this manner from the blocks 331*a* and 331*b* are the extraction of the specific sympathetic vasomotor signature, value 340.

This extracted sympathetic vasomotor signature can be used to quantify sympathetic vasomotion in ways that are useful to the clinician or patient. In the simplest manifestation, the patient's sympathetic vasomotor signature is obtained by extracting the bins identified as the specific sympathetic vasomotor signature 340 from the patient's data in the values 320, 322, and 324 to obtain the occurrence of the patient's sympathetic vasomotor signature as value 342. The value 342 is stored 344, for example, in a computer memory or data storage device such as a hard disk drive or FLASH memory, from where the value can be retrieved 346 later.

The value 342 and the data from the block 331*a* are also applied by normalizing the patient's sympathetic vasomotion to the mean sympathetic vasomotion from the healthy control data in 331*a* to determine a value 350. In the example process, the corresponding values of 342 are divided by the mean occurrence of each of the bins identified as part of the sympathetic signature in value 340 using the data from block 331*a*. The median across all bins is then used to express the patient's renal sympathetic vasomotion during the most recent time interval compared to healthy subjects. This can be useful in diagnosing pathology (e.g., patients with cardiovascular disease have increased renal sympathetic outflow) or identifying patients that might respond well to therapy (e.g., increased renal sympathetic drive may indicate a greater therapeutic response to renal nerve ablation).

The value 342, along with a stored prior sympathetic vasomotor signature value that is retrieved 346, if such a value is present, are applied by normalizing the patient's current sympathetic vasomotion to prior data to determine a value 352. In the example process, the corresponding values of 342 are divided by the occurrence of each of the bins identified as part of the sympathetic signature in value 340 using the data from block 331*a*. The median across all bins is then used to express the patient's renal sympathetic vasomotion during the most recent time interval compared to this prior level of renal sympathetic vasomotion. This allows for longitudinal assessment of this patient's sympathetic vasomotion over time. In this process, this could be used to assess response to a treatment (e.g., efficacy of renal nerve ablation in a hypertensive patient) or assess disease progression (e.g., increased renal sympathetic outflow portends a poor prognosis in heart failure patients).

The value 350 and the value 352 are then applied in a transfer function that quantifies the patient's sympathetic vasomotion to determine a value 360. In some implementations, the value 360 can be the example quantification of a sympathetic vasomotion signature 104 of FIG. 1.

Figure 4:
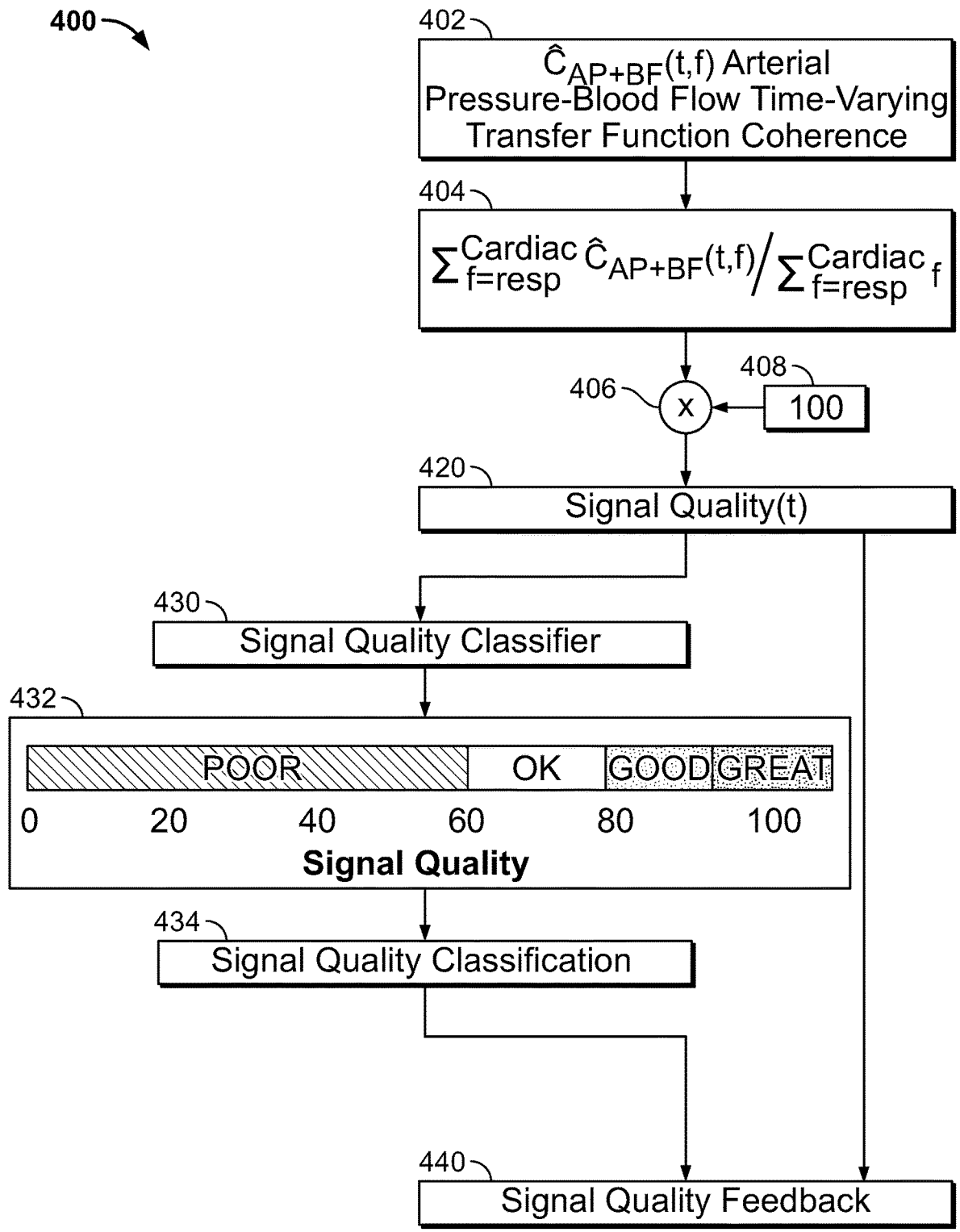
FIG. 4 is a flowchart depicting an example signal quality monitoring process.

FIG. 4 is a flowchart depicting an example signal quality monitoring process 400. In some implementations, the signal quality monitoring process 400 can be performed by the example signal quality quantifier 132 of FIG. 1.

Because blood flow passively follows blood pressure very closely at frequencies above those associated with the vascular control mechanisms, the coherence at these very high frequencies (i.e., ranging from the respiratory frequency to the cardiac frequency, approximately 0.4 Hz to 1 Hz in humans) can be used to assess the signal quality. The average coherence 402 of an arterial pressure-blood flow time-varying transfer function for frequencies ranging from the respiratory frequency to the cardiac frequency provides a value between 0 and 1. For example, the coherence 402 may be the example coherence 128 of FIG. 1.

The transformed 404 value is multiplied 406 by a factor 408 of one hundred to determine a signal quality value 420. For example, the coherence 402 may be a fractional value in a range of zero to one, and the signal quality value may be a value in a range of zero to one hundred.

The signal quality value 420 is received by a signal quality classifier 430. The classifier compares the signal quality value 420 to a collection of ranges 432 that represent a collection of signal quality classifications. In the illustrated example, signal quality values 402 ranging from zero to about sixty are classified as being "poor", values ranging from about sixty to about eighty are classified as being "OK", values ranging from about eighty to about ninety are classified as being "good", and values above about ninety are classified as being "great." The output of the signal quality classifier 430 is provided as a signal quality classification value 434.

The signal quality value 420 and the signal quality classification value 434 are then provided as signal quality feedback data 440. In some implementations, the signal quality feedback data 440 is the information that is output as the example signal quality feedback value 134 to the example user interface 106. The user interface 106 can update its display based on the signal quality feedback data 440. For example, for a signal quality value of "0.95", the user interface 160 may indicate a signal quality of "95" and "great." The display of signal quality will be discussed further in the description of FIG. 5.

Figure 5:
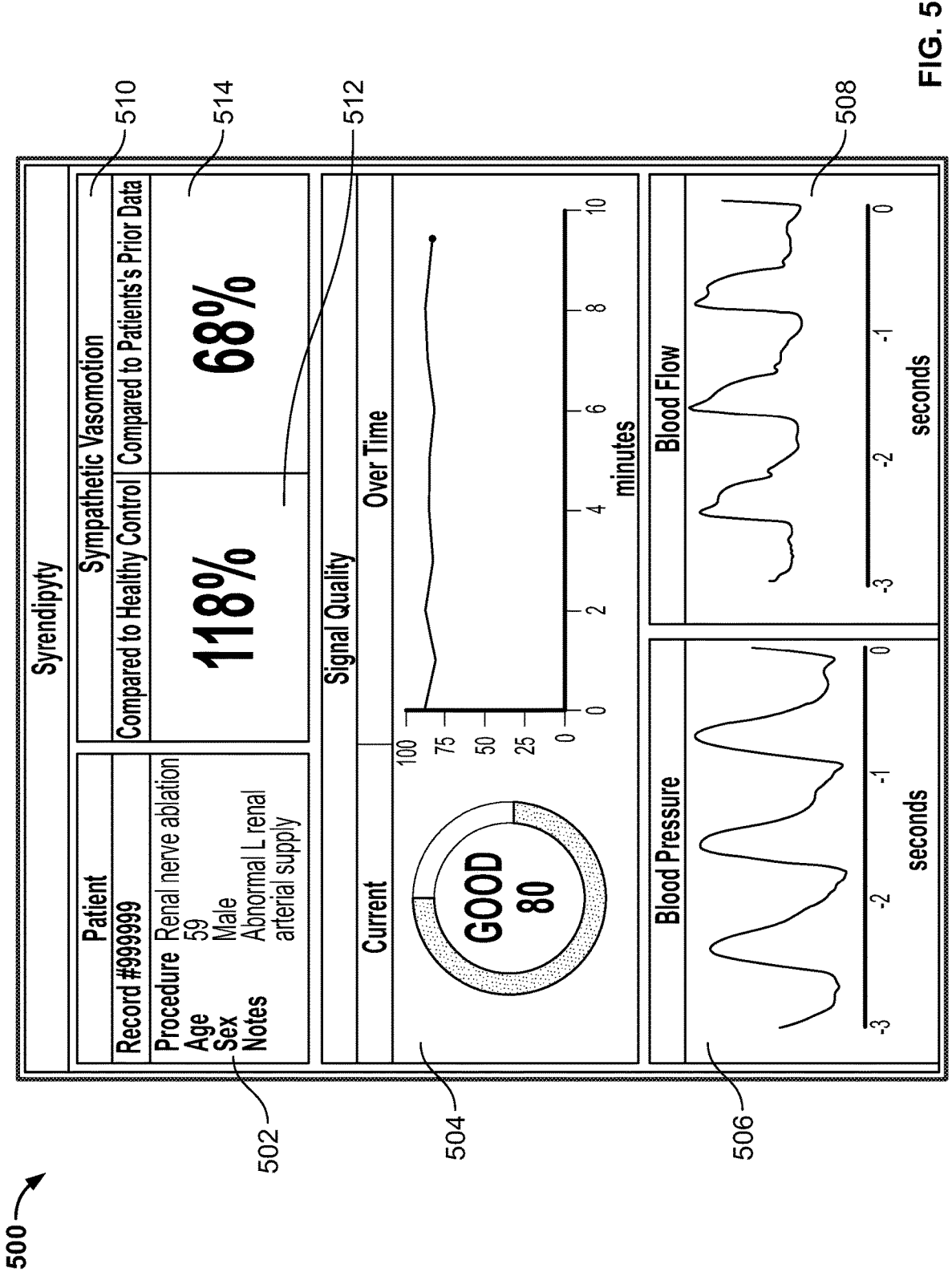
FIG. 5 is a screen shot of an example user interface of the sympathetic vasomotion identification and quantification systems in accordance with some embodiments.

FIG. 5 is an example screen capture of an embodiment of a user interface 500 of the sympathetic vasomotion identification and quantification systems provided herein. Other variations of user interface data displays are also envisioned.

In the depicted embodiment, the user interface 500 is configured to display patient data 502, which includes a patient identification number, a procedure description, patient age and sex, and notes. The user interface 500 is also configured to display a signal quality metric 504 (e.g., from the signal quality quantifier 132 as described in reference to FIG. 1). The user interface 500 is also configured to display a time-based blood pressure readout 506, and a time-based blood flow readout 508.

In the depicted embodiment, the user interface 502 is also configured to display one or more quantifications of sympathetic vasomotion 510. Here, the quantifications of sympathetic vasomotion include a percentage of sympathetic vasomotion compared to a healthy control 512 and a percentage of sympathetic vasomotion compared to the patient's prior data 514. For example, in some cases (without limitation) the embodiment of the user interface 502 shown in this figure may be displayed during a renal denervation procedure where the sympathetic vasomotion identification and quantification system 100 is employed to monitor treatment progress. In the depicted example, the one or more quantifications of sympathetic vasomotion 510 shows that the patient has 118% sympathetic vasomotion compared to a healthy control measured at a similar vascular bed, yet the patient's sympathetic vasomotion is 68% of the sympathetic vasomotion from the patient's prior data. A clinician performing a renal denervation procedure, for example, may use the one or more quantifications of sympathetic vasomotion 510 to decide when to end a procedure, or to determine a procedure's effectiveness. Additionally or alternatively, the user interface 500 may display an effectiveness quantification or a treatment recommendation based on the one or more quantifications sympathetic vasomotion 510.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A sympathetic vasomotion monitoring system, comprising:
   a user interface comprising a display; and
   a sympathetic vasomotion monitoring device comprising a sympathetic vasomotion quantifier and a signal quality quantifier, the sympathetic vasomotion monitoring device configured to:
   receive one or more blood pressure signals corresponding to a time-based series of blood pressure readings from a blood pressure monitoring device;
   receive one or more blood flow signals corresponding to a time-based series of blood flow readings from a blood flow monitoring device;
   calculate, by the sympathetic vasomotion quantifier, one or more quantifications of a sympathetic vasomotion signature based on: (a) the time-based series of blood pressure readings, (b) the time-based series of blood flow readings, and (c) a set of sympathetic vasomotion quantifier parameters comprising one or more types of physiological data;
   calculate, by the signal quality quantifier, a signal quality metric based on a coherence of an arterial pressure-blood flow time-varying transfer function, the signal quality metric being indicative of a quality of the one or more blood flow signals corresponding to the time-based series of blood flow readings; and
   output to the display: (i) the one or more quantifications of the sympathetic vasomotion signature, (ii) the time-based series of blood pressure readings, (iii) the time-based series of blood flow readings, and (iv) the calculated signal quality metric.

2. The sympathetic vasomotion monitoring system of claim 1, wherein the set of sympathetic vasomotion quantifier parameters comprises blood pressure data and blood flow data corresponding to a specific vascular bed.

3. The sympathetic vasomotion monitoring system of claim 2, wherein the specific vascular bed is a renal vascular bed.

4. The system of claim 1, wherein the set of sympathetic vasomotion quantifier parameters comprises blood pressure data and blood flow data associated with a disease or condition.

5. The system of claim 4, wherein the disease or condition is selected from a group consisting of: epilepsy, spinal-cord injuries, drug-induced autonomic dysfunction, pheochromocytoma, migraine, sleep apnea, adrenal insufficiency, mastocytosis, complex regional pain syndrome, chronic fatigue syndrome, alcoholism, carcinoid tumors, cancer, cyclic vomiting, neuroleptic malignant syndrome, hypertension, heart failure, cardiomyopathy, Takotsubo syndrome, chronic kidney failure, metabolic syndrome, insulin resistance, obesity, panic disorder, hemodynamic instability, hemorrhage, shock, and cerebrovascular accident.

6. The system of claim 1, wherein the set of sympathetic vasomotion quantifier parameters comprises blood pressure data and blood flow data associated with a treatment.

7. The system of claim 6, wherein the treatment is a renal denervation treatment.

8. The system of claim 1, wherein the sympathetic vasomotion monitoring device is further configured to:
   calculate a comparison between a patient's current sympathetic vasomotion and a healthy control; and
   output to the display the comparison between the patient's current sympathetic vasomotion and the healthy control.

9. The system of claim 1, wherein the one or more quantifications of the sympathetic vasomotion signature output to the display comprises a comparison between current sympathetic vasomotion of a patient and prior data of the patient.

10. A method for monitoring sympathetic vasomotion, comprising:
    receiving at a sympathetic vasomotion monitoring device:
    (i) one or more blood pressure signals corresponding to a time-based series of blood pressure readings from a blood pressure monitoring device and (ii) one or more blood flow signals corresponding to a time-based series of blood flow readings from a blood flow monitoring device;
    calculating, by a processor of the sympathetic vasomotion monitoring device, an arterial pressure-blood flow time-varying transfer function;
    calculating, by a sympathetic vasomotion quantifier of the sympathetic vasomotion monitoring device, one or more quantifications of a sympathetic vasomotion signature based on the arterial pressure-blood flow time-varying transfer function and a set of sympathetic vasomotion quantifier parameters comprising one or more types of physiological data;
    calculating, by a signal quality quantifier of the sympathetic vasomotion monitoring device, a signal quality metric based on a coherence of an arterial pressure-blood flow time-varying transfer function, the signal quality metric being indicative of a quality of the one or more blood flow signals corresponding to the time-based series of blood flow readings;
    outputting, to a display, the one or more quantifications of the sympathetic vasomotion signature and the calculated signal quality metric; and
    displaying, at the display, the one or more quantifications of the sympathetic vasomotion signature and the calculated signal quality metric.

11. The method of claim 10, wherein the set of sympathetic vasomotion quantifier parameters comprises blood pressure data and blood flow data corresponding to a specific vascular bed.

12. The method of claim 11, wherein the specific vascular bed is a renal vascular bed.

13. The method of claim 10, wherein the set of sympathetic vasomotion quantifier parameters comprises blood pressure data and blood flow data associated with a disease or condition.

14. The method of claim 13, wherein the disease or condition is selected from a group consisting of: epilepsy, spinal-cord injuries, drug-induced autonomic dysfunction, pheochromocytoma, migraine, sleep apnea, adrenal insufficiency, mastocytosis, complex regional pain syndrome, chronic fatigue syndrome, alcoholism, carcinoid tumors, cancer, cyclic vomiting, neuroleptic malignant syndrome, hypertension, heart failure, cardiomyopathy, Takotsubo syndrome, chronic kidney failure, metabolic syndrome, insulin resistance, obesity, panic disorder, hemodynamic instability, hemorrhage, shock, and cerebrovascular accident.

15. The method of claim 10, wherein the set of sympathetic vasomotion quantifier parameters comprises blood pressure data and blood flow data associated with a treatment.

16. The method of claim 15, wherein the treatment is a renal denervation treatment.

17. The method of claim 10, further comprising:
calculating, by the processor of the sympathetic vasomotion monitoring device, a comparison between a patient's current sympathetic vasomotion and a healthy control; and
displaying, at the display, the comparison between the patient's current sympathetic vasomotion and the healthy control.

18. The method of claim 10, wherein the displaying the one or more quantifications of the sympathetic vasomotion signature comprises displaying a comparison between current sympathetic vasomotion of a patient and prior data of the patient.

19. The method of claim 10, further comprising determining a treatment protocol based on the displayed one or more quantifications of the sympathetic vasomotion signature.

20. The method of claim 19, wherein the treatment protocol comprises a treatment time for a renal denervation procedure.

21. A sympathetic vasomotion monitoring system, comprising:
a user interface comprising a display; and
a sympathetic vasomotion monitoring device comprising a sympathetic vasomotion quantifier and a signal quality quantifier, the sympathetic vasomotion monitoring device configured to:
receive one or more blood pressure signals corresponding to a time-based series of blood pressure readings;
receive one or more blood flow signals corresponding to a time-based series of blood flow readings;
calculate, by the sympathetic vasomotion quantifier, one or more quantifications of a sympathetic vasomotion signature based on: (a) the time-based series of blood pressure readings, (b) the time-based series of blood flow readings, and (c) a set of sympathetic vasomotion quantifier parameters comprising physiological data;
calculate, by the signal quality quantifier, a signal quality metric based on a coherence of an arterial pressure-blood flow time-varying transfer function, the signal quality metric being indicative of a quality of the one or more blood flow signals corresponding to the time-based series of blood flow readings; and
output to the display the one or more quantifications of the sympathetic vasomotion signature and the calculated signal quality metric.

\* \* \* \* \*